United States Patent [19]

Begovac et al.

[11] 4,321,914
[45] Mar. 30, 1982

[54] PERCUTANEOUS CONDUIT HAVING PTFE SKIRT

[75] Inventors: Paul C. Begovac; William C. Bruchman, both of Flagstaff, Ariz.

[73] Assignee: W. L. Gore & Associates, Inc., Newark, Del.

[21] Appl. No.: 142,840

[22] Filed: Apr. 22, 1980

[51] Int. Cl.³ .................... A61B 19/00; A61M 5/00; A61M 25/00; A61M 27/00
[52] U.S. Cl. .................................. 128/1 R; 128/630; 128/214 R; 128/348; 128/350 R; 3/1
[58] Field of Search .................. 128/1 R, 2 R, 214 R, 128/348, 350 R, 422, 349 R; 3/1, 1.1

[56] References Cited

U.S. PATENT DOCUMENTS

| | | | |
|---|---|---|---|
| 3,663,965 | 5/1972 | Lee, Jr. et al. | 128/1 R |
| 3,699,956 | 10/1972 | Kitrilakis et al. | 128/348 |
| 3,964,470 | 6/1976 | Trombley | 128/2.1 E |
| 3,993,079 | 11/1976 | Gatztanondo | 128/347 |
| 3,995,644 | 12/1976 | Parsons | 128/418 |
| 4,014,347 | 3/1977 | Halleck et al. | 128/422 |
| 4,112,923 | 9/1978 | Tomecek | 128/1.3 |
| 4,183,357 | 1/1980 | Bentley et al. | 128/283 |

OTHER PUBLICATIONS

*Percutaneous Energy Transmission Systems*, Benedict Daly et al., Apr. 16, 1979, Publ. by U.S. Dept. of HEW, Publ. Health Serv., Natl. Int. of Health.

*Primary Examiner*—Robert Peshock
*Assistant Examiner*—Michael J. Foycik
*Attorney, Agent, or Firm*—Finnegan, Henderson, Farabow, Garrett & Dunner

[57] ABSTRACT

A percutaneous device to provide a path from the exterior of the epidermal tissue to interior body spaces and structures with a skirt of material with PTFE having an open microstructure for the ingrowth of epidermal and connective tissue.

12 Claims, 4 Drawing Figures

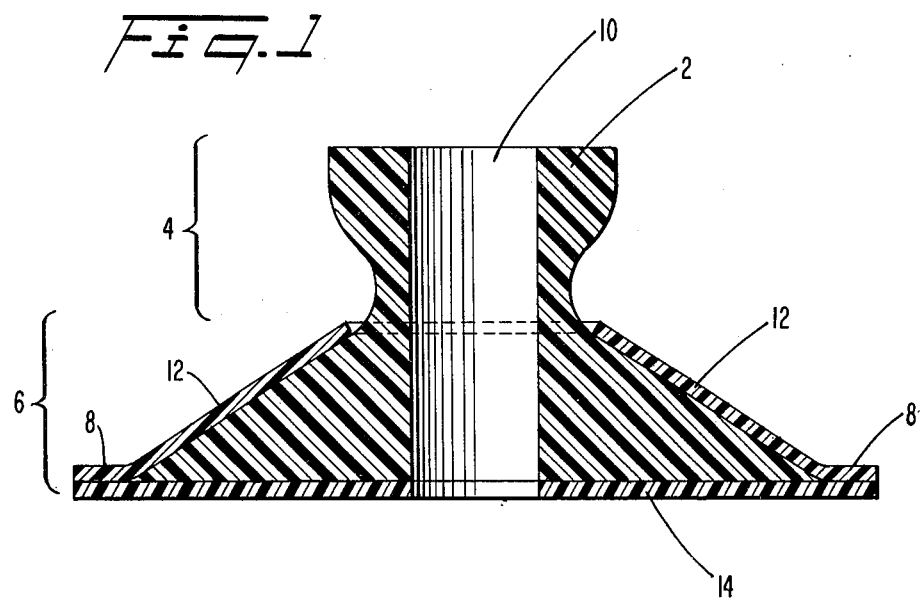
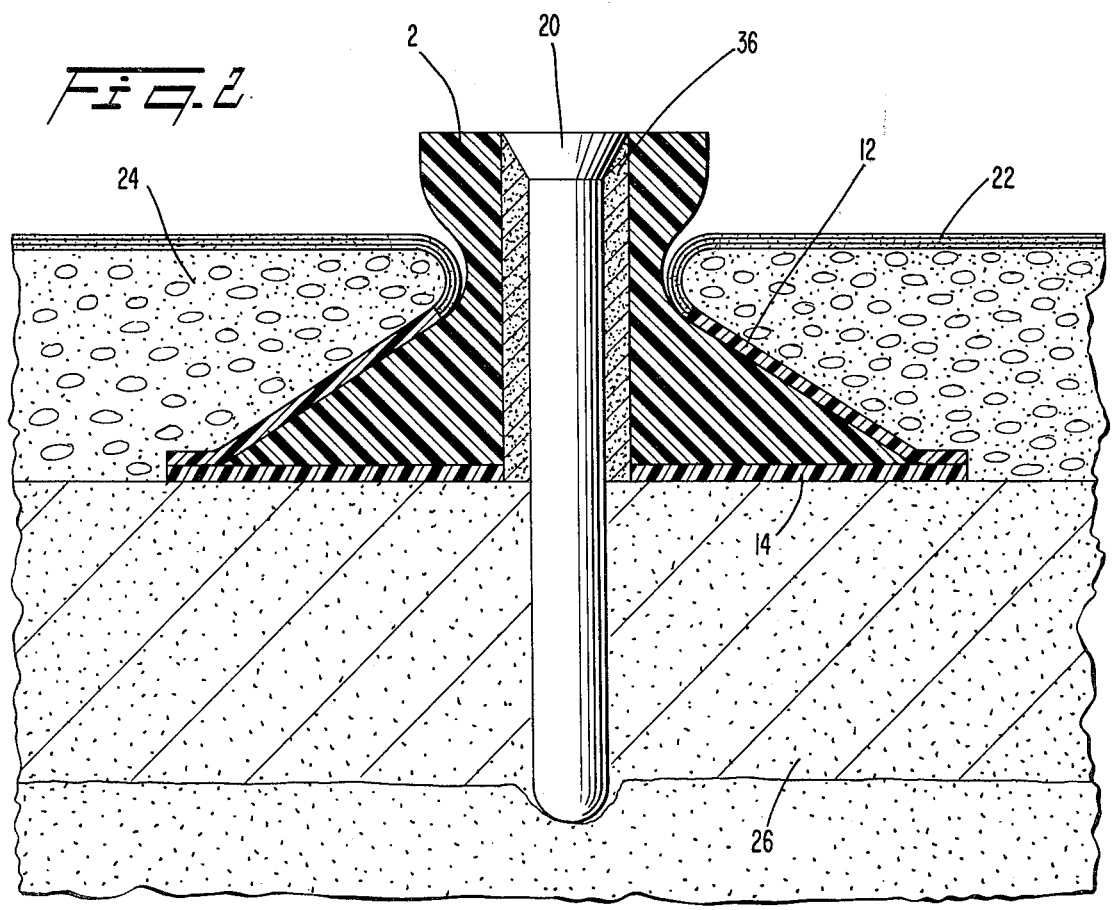

PERCUTANEOUS CONDUIT HAVING PTFE SKIRT

FIELD OF THE INVENTION

This invention relates to an improved percutaneous device which provides a port of entry for repeated long-term access to the interior regions of the body.

BACKGROUND OF THE INVENTION

A percutaneous implant is an object, foreign to the body, that has been placed through the skin to allow a port of entry to inner body spaces and structures. Temporary percutaneous access is required for a wide variety of procedures such as intra-venous fluid administration and hemodialysis. A number of these procedures also require chronic access. Specific examples of applications which benefit from a chronic percutaneous port include hemodialysis access, peritoneal dialysis access, power supply leads and fluid connections for artificial organs, charging for cardiac pacemakers, neuroelectric stimulation of nerves and/or muscles, artificial stimulation and monitoring in various brain implants.

Acute percutaneous access is routinely accomplished with devices constructed of silicone, polypropylene and polyurethane. These devices serve as a mechanism by which to gain blood access, wound drainage and many other applications. The chronic use of such devices, however, commonly results in infection and/or encapsulation of the device by the epidermis. Past attempts to overcome these problems have included a variety of devices constructed of various materials and have included both rigid and flexible devices. These previous attempts, however, have not provided completely satisfactory solutions. For example, rigid implants of various materials with base portions having a plurality of large diameter holes have been tried, the concept being to have tissue grow through the holes to secure the device in place. It is believed that there is inadequate growth of tissue into these devices to provide a completely satisfactory seal to exclude bacteria. The holes of these devices are also spaced so that good tissue ingrowth is unlikely to occur.

The basic design of prior art percutaneous devices includes a rigid central conduit of a biocompatible material attached to a rigid or semi-rigid fenestrated skirt. The conduit need only be large enough to pass the desired cannula size or electrical cable and still have sufficient wall thickness for structural strength. The dimensions of the conduit vary according to the specific application and the skirt thickness can be adjusted to give proper flexibility and tensile strength; the exact values are functions of the physical properties of the particular material used. The diameter of the skirt is normally only large enough to prevent excessive motion of the skin adjacent to the conduit and to distribute stresses over an area of intact skin.

Conduits have been made from a variety of materials including rigid epoxy, rigid polyurethane, polypropylene, polytetrafluoroethylene, carbon, polycarbonate, aluminum and titanium. Skirts have been made from flexible polyurethane, polypropylene, vitreous carbon fabric, dacron or nylon velour, and dacron mesh. Unsuccessful attempts have also been made to use expanded polytetrafluoroethylene (PTFE) as skirt material. These prior attempts specifically found that expanded PTFE having a fibril length of about $30\mu$ was unsuitable for skin interfacing due to insufficient interstitial connective tissue formation.

Previous devices have typically suffered from two major disadvantages:
1. Continuing high incidence of infection, due to inadequate sealing around the device. Inadequate sealing of the device into the body allows bacterial ingress and body fluid egress.
2. "Encapsulation" by the epidermis resulting either in isolation or extrusion of the implant from the body.

These phenomena have been a result of the physical properties of the materials used to fabricate the device and the physiological response when the device is placed in vivo.

BRIEF DESCRIPTION OF THE INVENTION

The percutaneous device of the present invention provides a safe, bacterial-resistant, long-term port of entry to the interior regions of the body whenever such entry would be required for any application.

This invention provides an improved percutaneous device which is virtually infection free and does not become encapsulated by the epidermis with resultant extrusion of the device. The percutaneous device has a button made of a biologically inert, non-porous material, having a top wall with a continuously curved perimeter, a pinched-waist-shaped side wall, and a bottom wall with a continuously curved perimeter larger in area than that of the top wall. This configuration provides a path to direct epidermal growth downward toward the healed subcutaneous surface. The device has an upper and lower skirt of a biologically inert material having an open microstructure for the ingrowth of epidermal and connective tissue. The upper skirt extends up the side wall from the perimeter of the bottom wall in laminar contact with the side wall to just below the minimum diameter of the pinched-waist-shaped side wall. The lower skirt is in laminar contact with the bottom wall and connected to the upper skirt adjacent the perimeter of the bottom wall. The skirt portion of the device is composed of expanded polytetrafluoroethylene (PTFE) with a microstructure of nodes interconnected by fibrils. This material, when there is a certain minimum node-fibril spacing, provides a framework for epidermal or fibrous tissue ingrowth. Such a material allows for three dimensional ingrowth into the skirt which is not available when holes are merely punched through an otherwise solid material even if the holes are closely spaced. The skirt portion is attached to the lower side wall and bottom wall of the button such that when the device is implanted, the skirt portion remains entirely below the skin while the nonporous material of the button above the pinched waist protrudes through the skin.

The present invention allows a path of entry for wires, tubes or mechanical systems for communication of information or performing operations on the interior regions of the body while preventing infection, body fluid egress and extrusion of the device from the body. Mechanical devices, such as valve mechanisms may be incorporated into the path provided by the present device to gain access to organs, glands and various fluid systems. Additionally, the percutaneous device can be used for dental implants, ureter exteriorization, various ostomy systems and electrodes to record or stimulate neurological responses.

DESCRIPTION OF THE DRAWING

FIG. 1 shows a cross-sectional view of the percutaneous device of the present invention.

FIG. 2 shows a cross-sectional view of the implanted percutaneous device with a removable plug and wires leading through the device.

DETAILED DESCRIPTION OF THE INVENTION AND DRAWING

In the early 1970's a new form of polytetrafluoroethylene (PTFE) was discovered. This new form of PTFE has a microstructure of nodes interconnected by fibrils. U.S. Pat. No. 3,953,566 describes a process for producing this product. One of the advantages of this material is that it can be rendered highly porous while exhibiting very high strength. Products made according to the teachings of U.S. Pat. No. 3,953,566 have found ready acceptance in the medical field where they have been widely used as vascular prostheses. A further advantage of the material is its extreme inertness and relative lack of chronic inflammatory response when implanted.

Figure 4:
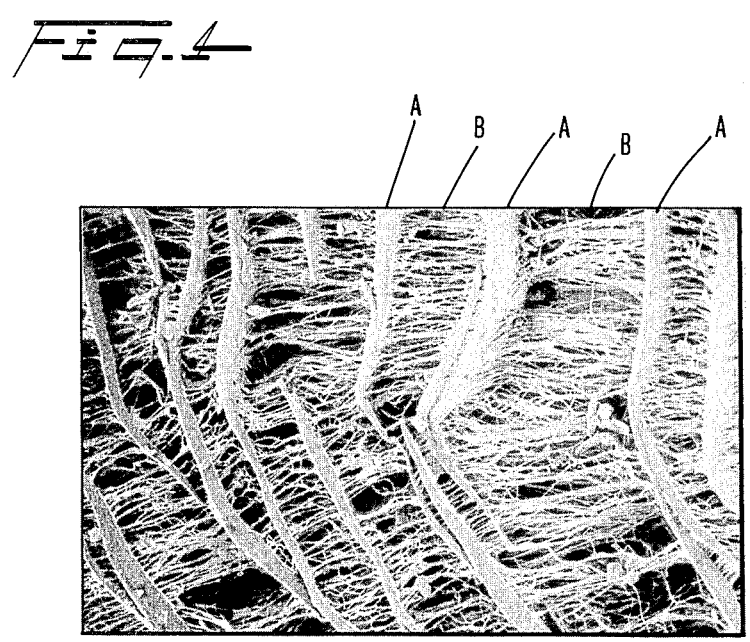
FIG. 4 is a scanning electron micrograph of expanded PTFE showing node, fibril spacing.

In discussing this invention, reference will be made to the porosity of the expanded PTFE. Internodal spacing and fibril length are synonymous terms referring to the distance between nodes (the length of the interconnecting fibrils) in the microstructure of the expanded PTFE. The measurement of fibril length is different from the term "pore size". "Pore size" is derived from an alcohol bubble point pressure test (ASTM E-128). This test is a relative measurement of the size of the largest pore in the material, whereas fibril length is obtained through direct inspection either with light or electron microscopy. FIG. 4 is a scanning electron micrograph of expanded PTFE having a node-fibril length of about 100$\mu$. The nodes in FIG. 4 are shown as A and the fibrils as B.

Attempts to produce a percutaneous device having a skirt of various materials including expanded PTFE, as produced by U.S. Pat. No. 3,953,566, bonded to a conduit of polycarbonate resulted in insufficient tissue ingrowth with resultant infection. The present invention differs from these attempts in at least one major aspect, the expanded PTFE used in the skirt has a fibril length in the range of 60 to 500 microns, preferably in the range of 100$\mu$ to 150$\mu$. In addition, the expanded PTFE skirt material of the present invention resides completely in subcutaneous tissue whereas in other attempts it has covered portions of the button which go through the skin surface.

The button segment is fabricated from a biologically inert, non-porous material. This segment may be machined, molded, cast or otherwise fabricated from full density PTFE, carbon, titanium, polycarbonate and other biologically inert materials. The button segment 2 as shown in FIG. 1 can be manufactured in a range of dimensions and sizes. The vertical height of the button, including the skirts, may be from about 0.20–1.25 inches and the diameter of the bottom wall of the button may be from about 0.40 to 4.00 inches. The low end of the size range has application as an electrical device whereas the larger devices can be used as a colostomy device. This button segment has a collar portion 4 and a flange portion 6.

The collar portion of the button serves the function of passing through the epidermal layer and guiding the proliferating epidermis down along the collar to the porous skirt. The collar, as depicted by FIG. 1, has a continuously curved perimeter at the top surface which can be in the range of about 0.15 inches to 2.00 inches. At the narrowest part of the pinched waist the collar has a continuously curved surface with a diameter of about 0.10 inches to 1.500 inches. While it has been found that a substantially hourglass-shaped collar portion, as depicted in FIG. 1, operates to perform these functions satisfactorily, it is believed that other designs for the collar are also functional. For example, the collar portion of the button may be shaped as a right circular cylinder or a right circular cone with its base as the top wall and a truncated apex joining the flange portion of the button.

The flange portion 6 of the button begins just below the pinched waist of the collar portion and is larger in diameter at the perimeter of the bottom wall than the collar. This flange may be conical in shape or even a flat plate joined to the collar. It has an upper surface and a bottom wall.

The flange serves to support the skirt material entirely below the skin. Further, it has a surface area larger than the top of the button on which to adhere the skirt material. It thus provides a large area for the contact of tissue with the skirt material. This area for ingrowth of tissue provides a barrier to bacterial ingress and body fluid egress as well as to distribute stresses on the device over an area larger than the top wall circumference of the collar.

The skirt material is manufactured from extremely porous expanded PTFE. This high porosity material allows rapid tissue ingrowth and the attachment of subcutaneous layers. Expanded PTFE used as the skirt material should have fibril lengths in the range of 60$\mu$ to 500$\mu$.

In the preferred embodiment of the present invention, the skirt segment is in two parts which are referred to as the upper skirt portion 12 and the lower skirt portion 14. The skirt portions of the device are formed of a material which is biocompatible. In addition, this material insulates the subcutaneous portion of the button so that no substantial amount of the area of the flange portion of the button is in direct contact with the interior region of the body. Since the expanded PTFE is biologically inert this eliminates chronic inflamatory or foreign body responses.

The material used for this skirt should have a thickness of about 0.01 to 0.25 inches. A hole, of appropriate size that corresponds to the collar diameter at the top surface, is cut out of the upper skirt 12. This upper skirt is then placed over the button segment and bonded to the side wall of the button just below the pinched waist of the collar portion by, for example, the use of medical adhesive. The adhesive should be of a type which will form a secure bond with the button material and be a biologically acceptable medical adhesive. Silicone based adhesives are of a generally acceptable type for this application.

The lower skirt portion 14 is bonded to the bottom wall of the button so that there is laminar contact between the bottom wall and the lower skirt. The edges of the two skirt portions extend beyond the perimeter of the bottom wall in the plane of the bottom wall and where they overlap each other 8 are also bonded together.

The microstructure of the skirt portion of the device facilitates the incorporation of tissues which seal the device from ingress of bacteria and egress of body fluids. As shown in FIG. 2, the epidermis 22 migrating down the collar grows into and "dead-ends" into the upper skirt microstructure rather than growing completely around the device and causing expulsion or isolation of the device.

The skirt material may be impregnated with a biologically active material such as an antibiotic or collagen or fibrin prior to implantation of the device. Introduction of biologically active materials, in this manner may serve to promote a quicker healing response.

Figure 3:
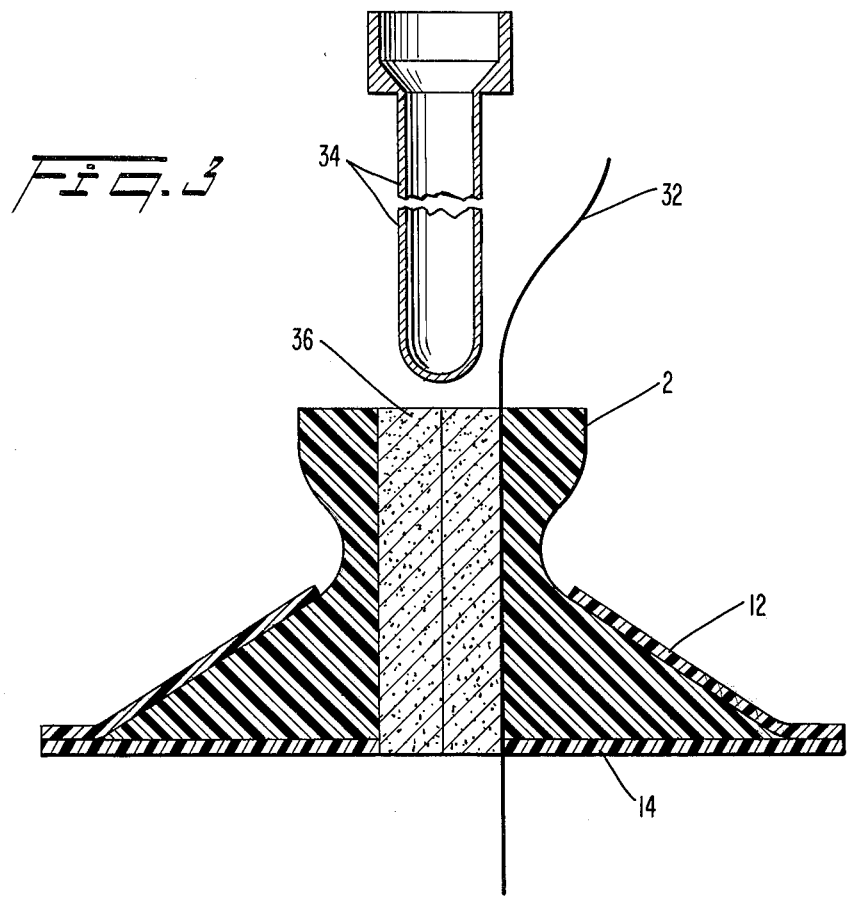
FIG. 3 shows a cross section of the percutaneous device with a wire affixed in a conduit through the device, a mechanical apparatus for use with the device and a self sealing valve.

The button of the device provides a path through which wires, tubes, conduits, valves or other mechanical devices may be placed, thereby connecting the interior regions of the body to the exterior regions. This path may be an open conduit 10 as shown in FIG. 1 through which access is obtained to the body and which is closed by a plug 20 shown in FIG. 2 which is tightly fitted within the conduit but removable when access to the body is desired. Alternatively, the device may be made with a conduit which is later permanently sealed after the desired wires, tubes or mechanical devices are inserted. Contacts such as shown in FIG. 3 by a wire 32 may lead into the body and may be secured to the button material by use of adhesives. As also depicted in FIG. 3, mechanisms such as a catheter 34 may be inserted through the device and the path may be closed by, for example, a self-sealing urethane slit valve 36. It is also possible to fabricate the device so that desired wires, conduits or mechanical devices are an integral part of the device.

The skirt on the bottom wall of the device may be formed with a hole to correspond to a conduit through the button or it may be a continuous sheet. If it does not have an opening through which wires, tubes or other devices can be inserted, such an opening may be made at the time a wire, tube or other device is inserted.

After device implantation, the healing response is characterized by the epidermis following the downward contour of the collar portion of the device and healing into the microstructure of the upper skirt. At this point, the epidermal movement stops and the epidermis becomes homeostatic. The epidermis sloughs squamous cells which accumulate in layers around the collar of the device. This mechanism serves as a continuous cleansing process. This epidermal response is significantly different from previous devices as the epidermis does not encapsulate the device but rather is incorporated into the microstructure of the skirt.

Within the skirt portion of the device, the healing response is characterized by the formation of viable connective tissues within the microstructure of the skirt material. This provides an active barrier to bacterial ingress and body fluid egress.

The combination of epidermal healing to the upper skirt of the device and the formation of viable connective tissues in the skirt from the dermis 24 and the subcutaneous tissue 26 as shown in FIG. 2 provides for incorporation of the percutaneous device as a part of the body, rather than becoming exteriorized. The epidermis and viable connective tissue within the microstructure of the skirt provides a barrier to bacterial ingress and body fluid egress as well as stabilizing the implant.

EXAMPLE I

A button segment was machined from full density PTFE to the configuration shown in FIG. 1. The dimensions were as follows: vertical height 0.415 inches; flange diameter at bottom wall 0.800 inches; collar diameter at the minimum of the pinched waist 0.260 inches; collar diameter at the top wall 0.360 inches. The PTFE flange segment was then etched in a sodium etchant for 15 seconds. Due to the properties of PTFE, bonding is difficult unless it is prepared to provide bonding sites on the button surface and any material which will perform this function may be used. A suitable etchant is available under the trade name TETRA-ETCH ™ available from W. L. Gore & Associates, Inc.

Following etching of the flange segment, the button was thoroughly washed with water and cleaned ultrasonically two times. The button segment was dried.

A tube of expanded PTFE with an average fibril length of 125 microns produced according to the teachings of U.S. Pat. No. 3,953,566 was split longitudinally. From this tube, sections approximately 5 cm×5 cm were cut. The thickness of this material was approximately 0.042 inches. One of the squares, which was to be used as the upper skirt, had a 0.250 inch diameter hole cut in it.

The flange portion of the button, from the perimeter of the bottom wall to just below the pinched waist of the side wall, was coated with a thin layer of a polyurethane adhesive sold under the trademark BIOMER available from Ethicon, Inc. The upper skirt portion was then placed over the collar of the button segment and secured completely covering the conical side wall on the flange portion of the button. The skirt material was carefully positioned on the flange portion to (1) provide the proper tension to prevent a crushing together of the node-fibril spacings of the skirt material and, (2) give good apposition against the collar. The device was then allowed to dry for 24 hours.

A second 5 cm by 5 cm square of the expanded PTFE forming the lower skirt was coated on the side which would attach to the bottom wall with a polyurethane adhesive and secured to the bottom wall of the button and to the portion of the upper skirt extending beyond the periphery of the bottom wall. The device was then allowed to dry for 24 hours.

UTILIZATION A

A percutaneous device prepared in a manner similar to that described in Example I, was implanted in a rabbit. The only difference was that the fibril length of the expanded PTFE was 90 microns. On removal after 60 days, the gross appearance of the tissue surrounding the percutaneous device was excellent, with no noticeable gross inflammation. Microscopically, an inflammatory response was observed at the button-skin interface, with gram-positive large diplococci present. The epidermal response to the solid PTFE button included an epidermal extension parallel to the solid PTFE button and perpendicular to the skirt segment. The epidermal extension was well attached to the upper skirt and exhibited a healthy appearance. Healthy fibrous tissue was observed in both layers of the skirt material extending beyond the periphery of the flange and on the bottom wall of the percutaneous device.

The general appearance of the access device was good, with epidermal and connective tissue healing in the 90μ skirt area. The button-skin interface demonstrated an inflammatory response, gram-positive large diplococci, and keratinized cell layers. The inflammatory response was confined to approximately 0.3 cm of skirt material on one side of the percutaneous button, and approximately 0.15 cm on the opposite side. Importantly, the bacteria were confined to the immediate region of the button-tissue interface and did not extend into the skirt material or surrounding tissue.

UTILIZATION B

Three percutaneous devices prepared in a manner similar to that in Example I using expanded PTFE with a fibril length of 125μ, were implanted in a rabbit. Two of the devices were topically challenged with a heavy inoculum of *Staphylococcus epidermidis*. One device was inoculated on the 75th, 77th and 79th days after implantation and the other device was inoculated on the 77th and 79th days after implantation. The third device remained untreated and served as a control. All devices were removed on the 82nd day after implantation.

Microscopic examination of the control device demonstrated an epidermal extension to the button-upper skirt material junction and healing within the upper skirt consisting of fibroblasts, collagen and functional capillaries and arterioles. Bacteria were not noted within or around the device. A healing response to the two challenged devices consisted of epidermal extension to or into the skirt material at the button-upper skirt junction and the formation of fibroblasts, collagen and functional capillaries and arterioles within the skirt material. In both challenged devices, bacteria were not observed to have penetrated the epidermal-upper skirt junction or the skirt material.

All devices exhibited a similar healing response including epidermal extension to or into the skirt material at the button-upper skirt junction. The skirt material was well healed with fibroblasts, collagen and functional capillaries and arterioles. The combined epidermal extension and healing in the 125μ skirt material created an effective "bacterial barrier" in the control device and in the two devices challenged with a common skin bacterium, *Staphylococcus epidermidis*.

UTILIZATION C

Two percutaneous devices were constructed of a full density PTFE tube with a 6 mm diameter bottom flange. The tube and flange were covered with 30μ fibril length expanded PTFE material. These devices differed from Example I in that the collar of the device coming through the skin was covered with the expanded PTFE material. The devices were implanted for a total of 62 days.

Both devices demonstrated a heavy inflammatory leukocytic response in the area of the epidermal—expanded PTFE interface. Healing of the epidermis into the interstices of the expanded PTFE was not noted. Attachment of the epidermis was generally lacking, with only slight adherence. Minimal collagen production was limited to the lower portion of the flange. The epidermis paralleled the device for a good distance with keratin accumulation along one-half the length of the devices. Unlike Utilization A, a tissue barrier was not established in the interstices of the expanded PTFE material.

In contrast to the healing sequence in Utilization A, these two devices demonstrate a random downward growth trend of the epidermis so that instead of abutting or healing into the expanded PTFE, the epidermis parallels the device without ingrowth or attachment. This type of response may encourage encapsulation of the device. Also, a tissue bed was not established within the interstices to accept epidermal attachment or ingrowth nor to provide a healthy tissue barrier to bacterial ingress.

What is claimed is:
1. A percutaneous device comprising:
   A. a button made of a biologically inert, non-porous material, said button including a top wall having a continuously curved perimeter, a pinched-waist-shaped side wall and a bottom wall having a continuously curved perimeter of larger area than said top wall, said button being capable of providing a path from the exterior of the epidermal tissue to interior body spaces and structures,
   B. an upper skirt and a lower skirt formed of expanded polytetrafluoroethylene having an open microstructure with a fibril length of 60 to 500 microns for the in-growth of epidermal and connective tissue,
       (i) said upper skirt extending up the side wall from the perimeter of said bottom wall in laminar contact with said side wall to an elevation just below the minimum diameter of said pinched-waist-shaped side wall; and
       (ii) said lower skirt being in laminar contact with said bottom wall and connected to said upper skirt adjacent the perimeter of said bottom wall.
2. The percutaneous device of claim 1 wherein the expanded polytetrafluoroethylene has fibril length of 100–150 microns.
3. The percutaneous device of claim 1 wherein the path is a conduit extending from said top wall to said bottom wall.
4. The percutaneous device of claim 3 having a removable plug for closing the conduit.
5. The percutaneous device of claim 4 including electrically conductive wires extending from said top wall to said bottom wall.
6. The percutaneous device of claim 3 wherein wires or tubes are secured in the conduit by adhesives.
7. The percutaneous device of claim 4 wherein the plug is composed of the same material as the button.
8. The percutaneous device of claim 1 wherein the button is made of full density polytetrafluoroethylene, carbon, titanium, silicon or polycarbonate.
9. The percutaneous device of claim 1 wherein the skirt is impregnated with biologically active material prior to insertion of the device in the body.
10. The percutaneous device of claim 1 wherein the device has a vertical height of 0.20–1.25 inches, a maximum flange diameter of 0.40 to 4.00 inches, a collar diameter of 0.10–1.50 inches at the pinched waist and 0.15–2.00 inches at the top surface.
11. The percutaneous device of claim 1 wherein the expanded polytetrafluoroethylene has a thickness of 0.01–0.25 inches.
12. The percutaneous device of claim 1 wherein a mechanical apparatus is incorporated in the path.

* * * * *